United States Patent [19]

Jespersen

[11] 4,343,316
[45] Aug. 10, 1982

[54] ELECTRONIC URINE FLOW MONITOR

[75] Inventor: Chris A. Jespersen, Fanwood, N.J.

[73] Assignee: C. R. Bard, Inc., Murray Hill, N.J.

[21] Appl. No.: 150,250

[22] Filed: May 16, 1980

[51] Int. Cl.³ .............................................. A61M 1/00
[52] U.S. Cl. .................................... 128/771; 128/762; 128/767; 128/295
[58] Field of Search ............... 128/771, 295, 760, 762, 128/767

[56] References Cited

U.S. PATENT DOCUMENTS

| | | | |
|---|---|---|---|
| 3,345,980 | 10/1967 | Coanda | 128/771 X |
| 3,769,497 | 10/1973 | Frank | 128/295 X |
| 3,776,231 | 12/1973 | Holbrook et al. | 128/768 X |
| 3,818,895 | 6/1974 | Stewart | 128/771 X |
| 3,888,236 | 6/1975 | Marx | 128/771 X |

OTHER PUBLICATIONS

Chambers et al., Med. and Biol. Engr., vol. 14, No. 6, pp. 665-670, Nov. 1976.
Haynes, B. W., A New Device for Measuring Urinary Output Hourly, JAMA, Oct. 15, 1960, p. 890.

*Primary Examiner*—Kyle L. Howell
*Assistant Examiner*—John C. Hanle
*Attorney, Agent, or Firm*—Dennison, Meserole, Pollack & Scheiner

[57] ABSTRACT

A urine flow monitor for displaying preferably in digital form total patient urine output and also urine flow rate. Urine from the patient passes through a catheter and into a calibrated volume chamber of special configuration which permits use even under conditions of vertical misalignment and wherein electronically controlled valve means are located both above and below the chamber and optical sensor means are provided above the chamber and below the top valve means. With the lower valve means closed, filling of the chamber takes place until the point where the urine level reaches the optical sensor at which time, by virtue of electronic control, the upper valve will close and the lower valve will open, allowing the urine to pass into a collection receptacle such as a urine drainage bag. Concurrently with the operation of the valve means, a signal is sent to a console monitor to record the volume dumped into the receptacle and also to commence operation of the flow rate recorder.

25 Claims, 5 Drawing Figures

ELECTRONIC URINE FLOW MONITOR

BACKGROUND OF THE INVENTION

The present invention relates broadly to the collection of urine output from hospital patients and for the measuring and monitoring of total urine output and urine flow rate. Conventionally, urine collection bags are routinely used for post-operative patients as well as those suffering from urological disorders. In use, the patient is first catheterized and the distal catheter end is then connected to the drainage bag through a length of tubing. The bag is normally suppported below the patient either from the bedrail or other support and the urine will drain by gravity from the patient through the catheter, the tubing and then finally into the bag.

Many of the prior art urine bags are provided with printed scales in the form of lines on the face of the bag to permit coarse visual monitoring of urine output. It is of course even possible with such bags to measure flow rate by use of a stop watch or other timing devices to measure the time interval between commencement of the sampling and the time when the urine level reaches a certain predetermined height in the bag and to then make appropriate calculations. An early example of a meter bag for urine is the U.S. Pat. No. 3,345,980 to Coanda. In this construction, urine flows from a catheter into an elongated rigid meter, the lower end of which connects to a separate storage container. A pinch valve prevents transfer of urine to the container until desired, and a meter overflow line is also provided. A somewhat more sophisticated arrangement is shown in Holbrook et al, U.S. Pat. No. 3,776,231, which discloses the use of two rigid containers located in tandem with a pivot valve joint to permit transfer of urine from a calibrated meter to a storage chamber. Using this arrangement, the ability to measure flow rate is simplified yet it still requires the presence of trained personnel and the use of a hand timer or the like, and of course calculation.

The present invention overcomes many of the problems in the prior art and provides automatic electronic means for measuring both total urine output as well as flow rate without constant monitoring by trained hospital personnel. The invention finds great utility in coronary care units, intensive care units, the treatment of burn patients, and for patients with kidney or other renal operations.

The principal advantages of the present invention over the known prior art are the increased accuracy of the measurements and the obviation of the necessity for utilizing trained personnel to constantly monitor and time flow operations. Further, problems in reading the scales on previous urine meters, including parallax errors, are not present.

Additionally, with the device of the present invention, it is not necessary for the monitoring unit to be installed on or adjacent the hospital bed with particular care as to alignment, since the device is designed to operate even under conditions of rather extreme misalignment from the vertical. It is not necessary for the hospital personnel to make any calculations or to do any timing whatsoever, all calculations being performed by the circuitry and digitally displayed on an easy-to-read monitor console. Further, if desired, alarm means may be provided on the console to give an indication of either low or high urine flow rates.

SUMMARY AND OBJECTS OF THE INVENTION

A urine flow monitor is provided for use in collecting and measuring patient urine output and flow rate using electronic circuitry. A special small volume double conical urine collection chamber is provided which is calibrated to hold a given volume of urine, preferably in the range of from 5 to 10 cubic centimeters. The calibrated chamber is located intermediate the catheter from the patient and the urine collection bag, and is supported on a control housing. Latex tubing connects from the chamber to the catheter on the input side and to the urine collection bag on the output side. Valve means are incorporated in the housing located above and below the calibrated chamber to close off flow alternatively at the input and at the output. An optical sensor is located immediately above the calibrated chamber and below the top valve means to sense the rise in urine level within the calibrated chamber and when the urine reaches the predetermined level established by the optical sensing means, the upper and lower valve means are actuated so as to close off fluid flow into the chamber and to permit dumping of the predetermined calibrated volume into the collection bag. Sensing means and circuitry external of the casing indicate the number of times the filled chamber is emptied and multiplies this by the chamber volume in order to provide a digital output of the total urine volume passed. Utilizing electronic timing means within the system, a separate digital indication of urine flow rate is provided.

It is a primary object of the present invention to provide an electronic urine flow meter which will indicate very precisely on an output console the total urine output of a patient and also provide accurate measurement of the flow rate of the urine.

It is a further object of this invention to provide a special support bracket and housing for a calibrated measuring chamber and associated valving means to permit filling and dumping of the calibrated chamber only at such times as the chamber fills to capacity.

It is a further object of the invention to provide an electronic urine flow meter which is extremely simple to operate and requires very little set-up time and calibration by hospital personnel and which can be read at a distance.

Yet a further object of the invention is to provide an electronic urine flow meter which is of relatively simple construction, has extremely high accuracy, and is secure, reliable and safe to the patient, and which may be used by nurses and technicians with a minimum of training.

Various other objects and advantages of my invention will be readily apparent from the following detailed description taken in conjunction with the drawings, in which an exemplary embodiment is shown.

DESCRIPTION OF THE PREFERRED EMBODIMENT

Figure 1:
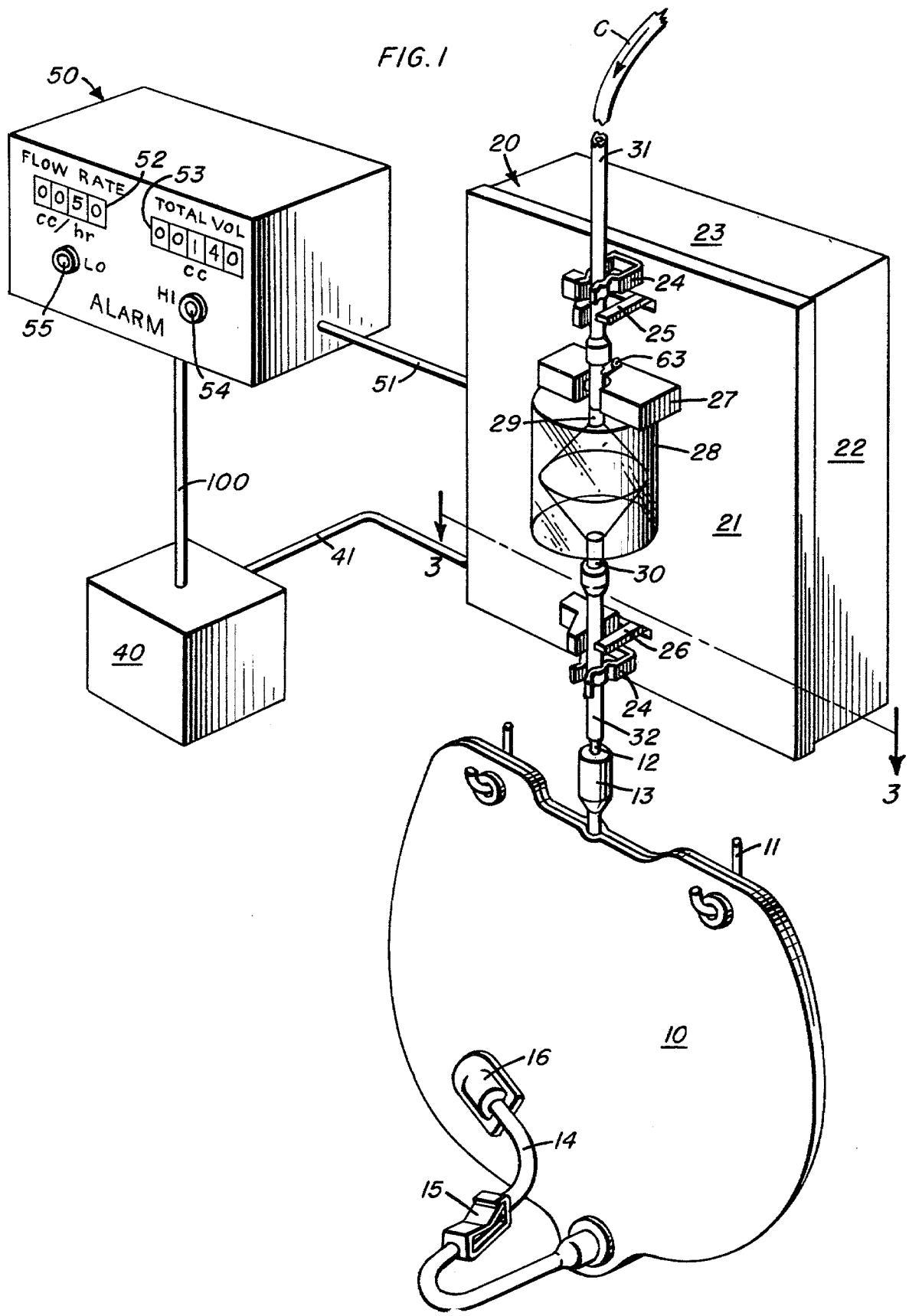
FIG. 1 is a perspective view of the various components of the electronic urine flow meter connected as a system.

Referring now to the drawings, the combination of elements is shown best in FIG. 1 and consists of a conventional urine drainage bag 10 adapted to be supported, as for example by hooks 11 secured adjacent to the patient's bed and preferably at a level below the same. The bag may be either of flexible plastic construction or formed of a hard clear plastic material as is conventional in the art, and the bag is provided with an inlet tube 12 which may pass through a drip chamber 13 to permit entry of the fluid to the interior of the bag. The bag may be drained by means of an outlet tube 14 which when not in use is pinched off by a metal or plastic tube clamp 15 and the end of the tube 14 is received within a pocket 16 formed on the bag. It will be understood that the details of the bag construction per se form no part of this invention, and any conventional collection receptacle may be used.

A control housing is shown generally at 20 and includes a front wall 21, side walls 22, a top and bottom wall 23, and a rear panel. Adjacent the top of the front face 21 and adjacent the bottom of the face, a pair of hose securing clips 24 are shown. These spring clips serve to receive and hold latex tubing both at the top and bottom of the device as further explained herein.

Also mounted on the front face 21 of the control housing is an upper hose pinch valve 25 and a lower hose pinch valve 26. These valves are identical in construction and will be described in greater detail herein. Located on the front face 21 below the upper valve 25 is a photoelectric source and detector housing 27.

The special volumetric calibrated chamber 28 of the invention is provided with a relatively narrow vertically extending transparent inlet tube 29 and an outlet tube 30. A latex tube 31 is frictionally secured at the top of the inlet 29 and a similar latex tube 32 is frictionally secured on the outlet 30. It will be understood that the tube 31 connects remotely to the catheter C which is attached to the patient and the latex tube 32 connects to the bag inlet tube 12.

Various circuits providing power and control for the photoelectric device as well as for operation of the hose pinch valves 25 and 26 are located in the remote chassis 40 which is connected by electrical cable 41 to the control housing 20.

A monitor console 50 is connected to the control housing 20 by means of a cable 51. Console 50 includes a digital display 52 for urine flow rate, preferably in cc's per hour, digital display 53 providing total volume of urine output measured in cc's, and it may also be provide with a high flow rate alarm 54 and a low flow rate alarm 55. The alarms may take various forms but preferably consist of LED devices which will be activated at times when the flow rate either exceeds or falls below a predetermined rate. It will also be understood that a strip chart recorder of conventional type may be provided either within the housing 50 or remote thereto to provide a permanent record of both total volume and flow rate.

Figure 2:
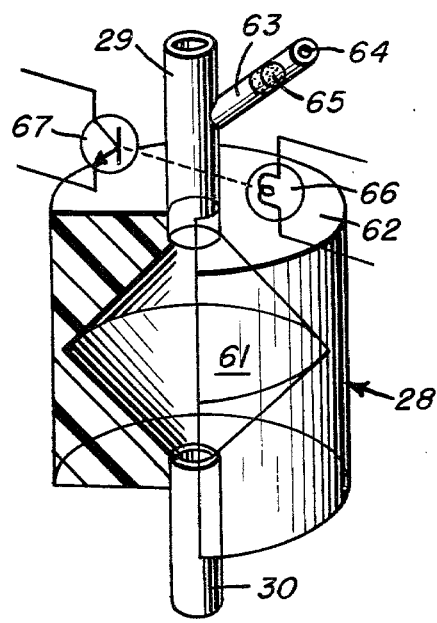
FIG. 2 is a detailed perspective partially in section of the calibrated chamber arrangement also showing the optical level sensing device in schematic form.

The calibrated urine chamber 28 shown best in FIG. 2 constitutes a very important part of my invention. Since extreme volumetric accuracy is required, the chamber shape should allow for a reasonable amount of vertical misalignment when the equipment is initially set up and the chamber shown in FIG. 2 of the device is relatively insensitive to such misalignment. It is important that the chamber fill up with no air space, hence a double cone shape has been found to be preferable. Two truncated right angle cones define the interior space shown at 61. The cone angles are approximately 90° or 45° to the vertical. This arrangement will permit vertical misalignment of up to 40° from the vertical axis for a chamber having a volume of 10 cubic centimeters. While the calibrated chamber 28 may be made of any selected material, it is preferable to form it of hard transparent plastic, and in the preferred form shown in the figure, the outer configuration is cylindrical and formed with an integral upperwardly and downwardly extending inlet tube 29 and outlet tube 30. Spaced above the top surface 62 of the chamber is a short vent pipe 63 open at its end 64 and provided internally therein with a microporous filter 65. This arrangement allows venting of the chamber to facilitate emptying of the interior thereof when the lower pinch valve 26 is opened.

The configuration of the calibrated chamber has been particularly selected so that for the physical limitation of its overall size it allows the largest theoretical volume for complete filling and emptying. Since the accuracy of the device is proportional to the size of the sample, maximizing the sample size is desired, and the present design allows maximization of such sample size. It is of course possible to use other shapes including spherical or cylindrical volumes if neither high accuracy up to the 40° tilt angle nor maximum volume are required.

Figure 4:
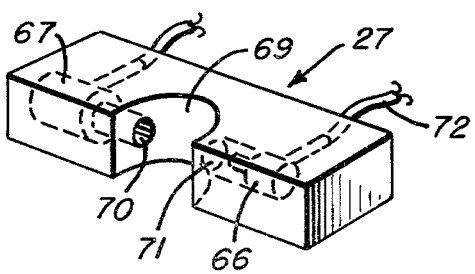
FIG. 4 is a perspective showing the optical photodetector sensor housing.

It is further important that the inlet 29 be made of relatively small diameter in order to provide greater accuracy with respect to the optical light sensing device shown schematically in FIG. 2 which includes a light source 66 and a photodetector 67. It will be seen that the light path extends through the transparent inlet 29 between the top surface 62 of the calibrated chamber and the vent 63. Additional details of the light sensing device are shown in FIG. 4 wherein the light source 66 and the photodetector 67 are located within the sensor housing 27 affixed to the front face 21 of the control housing. The sensor housing 27 includes a central arcuate cutout 69 and longitudinal bores 70 and 71 extend medially into the cutout 69 to permit passage of the light from the source 66 to the detector 67. Appropriate leads as shown at 72 connect to the control circuit. It will be noted that when the device is set up for use, the calibrated chamber will be located below the sensor housing so that the inlet 29 will extend within the arcuate cutout 69. Flow of urine into the calibrated chamber will cause filling thereof until such time as the urine level reaches the dotted line shown in FIG. 2 which is of course the line indicating passage of light between the source and the photodetector. At this point, the light will be occluded and various control circuits will operate as noted further herein.

Figure 3:
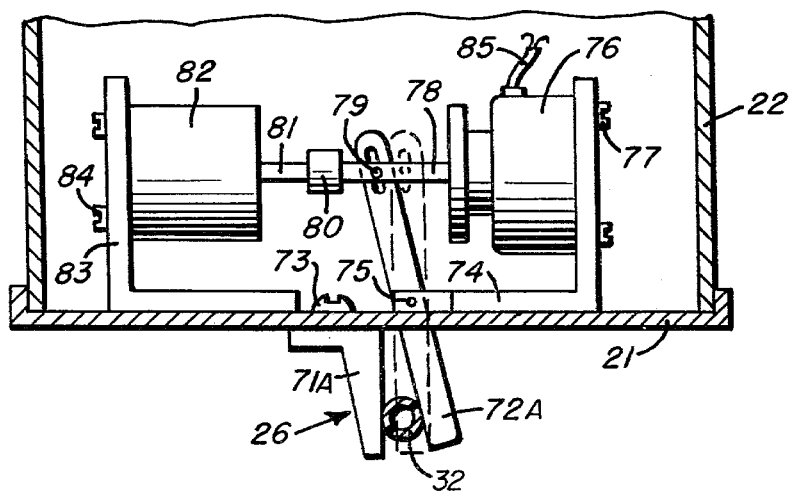
FIG. 3 is a cross-section taken through line III—III of FIG. 1 and showing the solenoid operation of the pinch valve.

The pinch valve means 25 and 26 are identical in construction and are shown in greater detail in FIG. 3. Valve 26 is shown and includes a fixed anvil or jaw 71A and a pivoted jaw 72A. Jaw 71A is secured to the top face 21 of the control housing by means of a screw 73. The movable jaw 72A is pivoted to a bracket member 74 as shown at 75. The open position of the pinch valve is shown in full lines and the closed valve position is shown in dotted lines in FIG. 3. In order to actuate the pivoted jaw 72A, a solenoid 76 is mounted by the bracket 74 to the inner surface of the top face 21. Screw members 77 secure the solenoid to the bracket. A solenoid control rod 78 extends from the solenoid itself and a pin member 79 pivotally mounts the end of the jaw 72A to the rod through a slot connection. The rod extends to a coupling 80 from which a shaft 81 extends to an Airpot 82 mounted on the bracket 83 by means of screws 84. The Airpot is a conventional commercial device which acts as a dashpot to cushion the movement of the solenoid control rod and to reduce the snapping action thereof, and the noise level associated with the actuation of the device. It will be understood that when the solenoid 76 is actuated through the contacts 85 which are connected to the control circuit, the control arm will move from its extended position to the retracted position so that the pivoted jaw member 72A will move from the full line to the dotted line position thereby pinching the latex tubing 32 to restrict any further passage of fluid therethrough.

It will further be understood that the pinch valve 25 operates in exactly the same manner as that depicted for the valve 26, except that its operation is reversed. That is, the valve 25 will be closed when the valve 26 is opened and vice versa.

While pinch valves are shown in the preferred embodiment of the invention, it will be understood that any other valve means which may be controlled externally and by electrical means may be used.

It is further contemplated that upper pinch valve 25 could even be omitted if desired, although the resulting readings will not be as accurate in such case.

Figure 5:
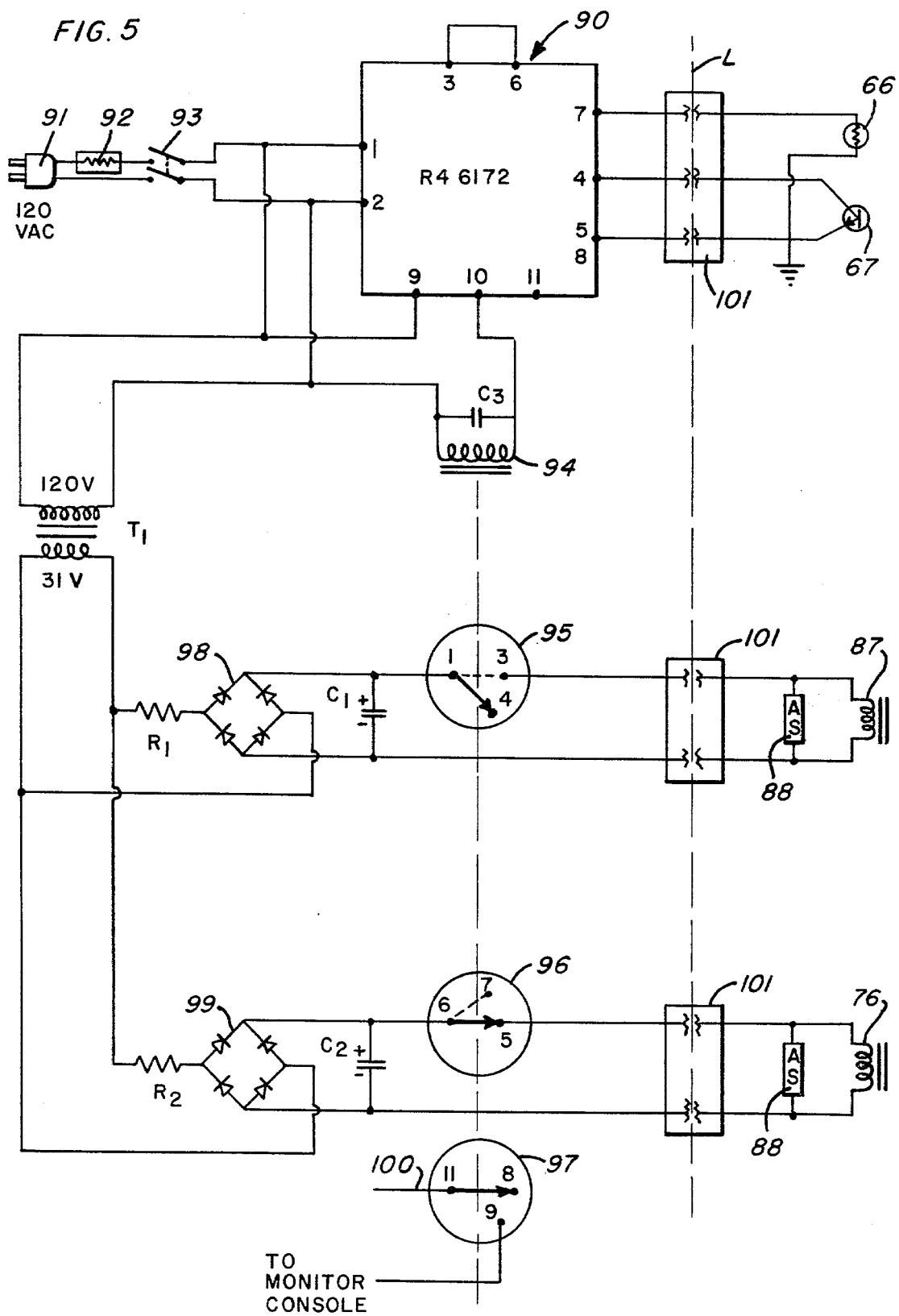
FIG. 5 is a schematic of the circuit arrangement and relay system for the light source and the upper and lower pinch valve solenoids.

The pinch valve control and optical sensor circuit is shown in FIG. 1 located within the housing 40 although it should be understood that all of the circuitry constituting this control may be physically located within the monitor console 50 if desired. The details of the pinch valve control and optical sensor circuit are shown schematically in FIG. 5. The circuit elements to the right of the dotted line L are physically housed within the control housing 20 and include the light source 66 and the photodetector 67, the upper solenoid 87, and the lower solenoid 76. Additionally, are suppressors 88 are incorporated in the lines to the solenoids for safety purposes.

The heart of the control consists of a photoelectric control with time delay shown at 90. The particular unit depicted in the drawing is the Model R46172 Time Delay Photoelectric Control manufactured by Skan-A-Matic of West Elbridge, New York. This device takes power from a 120 V AC source as shown at 91 through a fuse 92 and a master switch 93 to the input terminals 1 and 2 of the device. The unit 90 provides light source power as indicated, amplifies the photodetector signal and utilizes its output to switch a load by virtue of a relay 94. The contacts of the relay which are employed for operation of the upper and lower solenoids are shown at 95 and 96. A further control signal contact is shown at 97 and will be described later herein.

The normal position of the relay contact arms is shown in full lines in the figure, however when the relay is powered the arms will shift to the dotted line positions as shown.

Power to the solenoids is taken through a step-down transformer shown at T1. In this case, the line voltage has been stepped-down to approximately 31 volts AC in order to provide a safety factor since the device will be used in proximity to a patient. Resistors R1 and R2 are selected at approximately 50 ohms and are connected to full wave rectifiers 98 and 99. The condensers shown at C1 and C2 are preferably 9000 μf. Condenser C3 across the relay is selected at 0.1 μf @ 400 volts (nonelectrolytic). The relay contact 97 is connected by leads 100 to the monitor console 50 as shown in FIG. 1. Note that contact 97 is a simple on-off switch and when actuated serves to transmit a signal to the totalizer and flow rate circuits in the controller console. Appropriate logic debouncer means may be provided for the contacts if desired, all as well known to those skilled in the art.

Reference character 101 indicates that all of the leads from the photoelectric controller 90, the relay contacts 95 and 96 are physically housed within the same shielded cable. Connector means are provided as shown so that the control housing 20 may be disconnected from the circuit when required for transportation and/or storage.

The logic circuits incorporated in the control monitor 50 may take various forms, all as well known to those skilled in the art, and play no part in the present invention. It will be understood that control signals from the relay contact 97 will serve to actuate the total volume count readout 53 and through stored program information in the console to actuate the flow rate counter 52. Further, circuitry which may be manually adjusted to the operator will actuate alarms 54 and 55 at such times as the flow rate falls below or above certain preset limits.

OPERATION OF THE SYSTEM

After the system as depicted in FIG. 1 has been installed at the bedside of the patient, and the patient has been catheterized, the console monitor may be reset so that the total volume and flow rate displays are each zeroed. Thereafter, the system is turned on and as will be noted from the schematic diagram in FIG. 5 under this condition, by virtue of the relay contact 96, the lower solenoid 76 will be actuated and the bottom pinch valve 26 will be closed, thereby allowing any fluid passing from the catheter into the tube 31 to collect within the calibrated chamber at 28. The chamber is sized so that the volume of the container itself and the tubing above the lower pinch valve 26 to the point where the sensor beam passes through the inlet tube 29 will be a precise figure such as from 5 to 10 cubic centimeters. As urine builds up within the calibrated chamber, it can be visually monitored. When the level of the fluid reaches the inlet 29 which is constricted, further accumulation will cause a rather rapid rise in the level within the inlet and at the point where the fluid level reaches the light beam passing between the source 66 and the photodetector 67, the same will be occluded. This will be sensed by the unit 90 and will cause immediate actuation of the relay 94 and the contacts 95, 96, and 97.

Simultaneously, the contact 95 will switch to the dotted line position 3 serving to actuate the solenoid 87 and to close the top pinch valve 25 to thereby block further passage of urine into the calibrated chamber. At the same time, the contact 95 will move to the open position against the terminal 7 and the solenoid 76 will be deactuated thereby allowing pinch valve 26 to open, dumping the contents of the calibrated chamber into the urine bag 10. The relay contact 97 will be switched to the dotted line position 9 thereby closing the circuit, sending a signal to the monitor console, wherein the totalizer will count one volume, which, for the purpose of explanation, will be assumed to be 10 cubic centimeters. Hence, the digit 10 will appear in the display 53. This initiation will also serve to actuate the flow rate meter to provide the flow per unit of time. The control unit 90 is provided with a timer so that after the fluid level starts receding to permit passage of light between the source 66 and the detector 67, the relay will not be actuated until a sufficient predetermined period of time has passed to allow full dumping of the contents of the calibrated chamber. After this period of time has elapsed, the system will revert to its initial condition wherein the relay 94 is de-energized causing each of the contacts 95, 96 and 97 to return to their normal positions wherein the lower pinch valve 26 will be closed and the upper pinch valve 25 will be opened, and the signal from the contact 97 will cease.

The apparatus is designed with built-in safety factors. For example, if there is a master power failure in the hospital or a power failure in the lines running to the equipment, it will not cause backup of urine past the chamber 28 back into the catheter which of course would present serious problems to the patient. With the circuit of the present invention, loss of power will immediately cause the lower pinch valve 26 to open since the lower solenoid 76 will be deactivated. This will permit passage of the urine directly into the bag 10.

It will be apparent that the apparatus described herein has utility apart from the hospital environment for the electronic monitoring of urine flow. In fact, the apparatus can be used in many other fields, as for example the monitoring of fluid flow in the laboratory or in various chemical processes involved in the manufacture of products. While the invention has been described principally for monitoring the urine flow, the invention is not so limited except as defined in the appended claims.

It will be readily apparent to those skilled in the art that various other modifications and changes may be made in the circuits and in the mechanical details which come within the spirit of the invention and all such changes and modifications coming within the scope of the claims are embraced thereby.

I claim:

1. An electronic urine flow monitor comprising,
    a calibrated volume urine collection chamber having top and bottom portions in the shape of truncated cones, the narrow open ends thereof being at the top and bottom extremities of the container,
    first tubing means connecting said top narrow end of the chamber to a patient and adapted to pass urine to said chamber,
    a urine drainage reservoir,
    second tubing means connecting said bottom narrow end of the chamber to said reservoir,
    first remote control normally closed valve means normally acting to prevent flow through said second tubing means, second remote control normally open valve means between said chamber and the patient and closable to block flow through said first tubing means when said first valve means is open,
    sensor means for sensing the filling of said double conical chamber,
    indicator means for displaying total urine output, and
    control means connected to said sensor means, said first and second valve means, and said indicator means for closing said second valve means and opening said first valve means to dump the contents of said chamber into said reservoir, and advancing said urine output display when said sensor means indicates the filling of said chamber.

2. A monitor as defined in claim 1, and further including timer reset means for reclosing said valve means after chamber emptying.

3. A monitor as defined in claim 1, and further including means for displaying urine flow rate connected to said control means.

4. A monitor as defined in claim 3 and further including an alarm means to indicate a flow rate above a preset maximum value.

5. A monitor as defined in claim 3 and further including an alarm means to indicate a flow rate below a preset minimum value.

6. A flow monitor as defined in claim 5 wherein said second valve means is mounted on said control housing, a second solenoid for operating said second valve means and connected to said relay, whereby actuation of said relay will operate said second solenoid and close said second valve means.

7. A monitor as defined in claim 1 wherein said sensor means comprises a photoelectric beam source and a photodetector, the beam passing from said source across said first tubing means to said photodetector whereby a rise in urine volume across said beam will occlude the passage of light to actuate said control means.

8. A monitor as defined in claim 7 wherein at least part of said second tubing means has collapsible walls, said first valve means comprising a pair of jaws about said part of said second tubing means and adapted to pinch said part to prevent urine flow.

9. A monitor as defined in claim 8 wherein said control means includes a relay, a solenoid connected to said relay and to said jaws wherein an occlusion of said sensor means will actuate said relay causing operation of said solenoid and said jaws.

10. A monitor as defined in claim 1 and further including a transparent small diameter inlet tube extending from the top of said chamber and adapted for connection to said first tubing means.

11. A monitor as defined in claim 10, and further including a vent in said small diameter inlet tube.

12. An electronic patient urine flow monitor comprising,
    a console for visually displaying total urine volume measured,
    a control housing located adjacent to the patient and including a calibrated volume chamber mounted thereon and having top and bottom portions in the shape of truncated cones, the narrow open ends thereof being at the top and bottom extremities of the container, an inlet tube connected from said patient to said top narrow end of the chamber,
    a urine drainage bag,
    an outlet tube connected from said bottom narrow end of the chamber to said drainage bag,
    first normally closed valve means mounted on said control housing and normally closing said outlet tube, second normally open valve means between said chamber and the patient and closable to block flow through said inlet tube when said first valve means is open,
    optical sensor means on said housing adjacent the top of said chamber to sense filling thereof and emit a signal,
    control circuit means including a relay, a solenoid connected to said relay for operating said first and second valve means, and control means operable by said sensor means signal to actuate said relay to open said first valve means and close said second valve means, and signal means operated by said relay when actuated for advancing the urine volume display.

13. A flow monitor as defined in claim 12 and further including means for displaying urine flow rate in said console.

14. A flow monitor as defined in claim 12 wherein the volume of said chamber is between 5 and 10 cubic centimeters.

15. A flow monitor as defined in claim 12 and further including a vent leading into the top of said chamber.

16. An electronic fluid flow monitor comprising,
a calibrated volume fluid collection chamber having top and bottom portions in the shape of truncated cones, the narrow open ends thereof being at the top and bottom extremities of the container,
first tubing means connecting said top narrow end of the chamber to said reservoir,
first remote control valve means normally being closed and acting to prevent flow through said second tubing means, second normally open remote control valve means between said chamber and said source of fluid and closable to block flow through said first tubing means when said first valve means is open,
sensor means for sensing the filling of said chamber, indicator means for displaying total fluid output, and control means connected to said sensor means, said first and second valve means, and said indicator means for closing said second valve means and opening said first valve means to dump the contents of said chamber into said reservoir, and advancing said fluid output display when said sensor means indicates the filling of said chamber.

17. A monitor as defined in claim 16, and further including timer reset means for reclosing said first valve means and opening said second valve means after chamber emptying.

18. A monitor as defined in claim 16, and further including means for displaying fluid flow rate connected to said control means.

19. A monitor as defined in claim 18 and further including an alarm means to indicate a flow rate above a preset maximum value.

20. A monitor as defined in claim 18 and further including an alarm means to indicate a flow rate below a preset minimum value.

21. A monitor as defined in claim 16 wherein said sensor means comprises a photoelectric beam source and a photodetector, the beam passing from said source across said first tubing means to said photodetector whereby a rise in fluid volume across said beam will occlude the passage of light to actuate said control means.

22. A monitor as defined in claim 21 wherein at least part of said second tubing means has collapsible walls, said valve means comprising a pair of jaws about said part of said second tubing means and adapted to pinch said part to prevent fluid flow.

23. A monitor as defined in claim 22 wherein said control means includes a relay, a solenoid connected to said relay and to said jaws wherein an occlusion of said sensor means will actuate said relay causing operation of said solenoid and said jaws.

24. A monitor as defined in claim 16 wherein said chamber has the shape of two truncated cones joined at their bases, and a transparent small diameter inlet tube extending from the top thereof and adapted for connection to said first tubing means.

25. A monitor as defined in claim 24 and further including a vent in said small diameter inlet tube.

* * * * *